United States Patent [19]
Brazeau et al.

[11] Patent Number: 5,834,418
[45] Date of Patent: Nov. 10, 1998

[54] PROCESS FOR THE PREPARATION OF PLATELET GROWTH FACTORS EXTRACT

[75] Inventors: Paul Brazeau; Thierry Abribat; Michel Ibea; Michèle Boushira, all of Montréal, Canada

[73] Assignee: Theratechnologies, Inc., Montreal, Canada

[21] Appl. No.: 618,560

[22] Filed: Mar. 20, 1996

[51] Int. Cl.⁶ .......................... A61K 38/17; C07K 14/435
[52] U.S. Cl. .................................. 514/2; 514/12; 514/21; 530/380; 530/422
[58] Field of Search .................................. 530/380, 422; 514/12, 21, 2

[56] References Cited

PUBLICATIONS

Assoian RK et al., *J. Biol. Chem.*, 1983, 258:7155–7160.
Carter et al., *In Growth Factors and Other Aspects of Wound Healing: Biological and Clinical Implications*, Alan R. Liss, Inc., 1988, 303–317.
Greenhalgh DG et al., *Wound. Rep. Reg.*, 1993, 1:69–81.
Knighton et al., *In Growth Factors and Other Aspects of Wound Healing: Biological and Clinical Implications*, Alan R. Liss, Inc., 1988, 319–329.
Knighton et al., *Ann. Surg.*, 1986, 204:322–330.
Lowry method, *J. Biol. Chem.*, 1951, 193:265–275.
Lynch SE et al., *J. Clin. Invest.*, 1989, 84:640–646.
Sara VR et al., *Physiol. Rev.*, 1990, 70:591–614.
Stroobant P & Waterfield MD, *EMBO J.*, 1984, 12:2963–2967.
Assoian et al. *J. Biol. Chem.*, vol. 258:7155–60 (1983).
Carter et al., In Growth Factors and Other Aspects of Wound Healing, Alan R. Liss, Inc., 1988, pp. 303–317.

*Primary Examiner*—Cecilia J. Tsang
*Assistant Examiner*—Anish Gupta
*Attorney, Agent, or Firm*—Evenson, McKeown, Edwards & Lenahan, P.L.L.C.

[57] ABSTRACT

The present invention relates to a process for the preparation of porcine platelet-extract containing matured growth factors, which comprises the steps of: a) centrifuging whole porcine blood at about 1000 g to about 5000 g to isolate the platelets from the platelet-rich-plasma; b) resuspending the isolated platelets of step a) in Plasma-Lyte A and centrifuging to concentrate the platelets; c) washing the concentrated platelets of step b); d) lyophilizing the washed platelets of step c); whereby causing lysis of the platelets and producing the platelet extract in optimal amount.

8 Claims, 12 Drawing Sheets

PROCESS FOR THE PREPARATION OF PLATELET GROWTH FACTORS EXTRACT

BACKGROUND OF THE INVENTION (a) Field of the Invention

The invention relates to a process for the production of platelet extracts derived from whole porcine blood and their clinical uses in wound dressing.

(b) Description of Prior Art

Wound healing is a complex cascade of cellular and biochemical events which lead to wound closure and repair of tissues. Three successive phases are classically distinguished in the wound healing process:

1) the inflammatory phase, which corresponds to increased vascular permeability and migration of leukocytes and macrophages;
2) the proliferative phase, characterized by fibroblast proliferation and collagen synthesis, resulting in granulation tissue formation; and
3) the remodeling phase, where collagen and granulation tissue rearrangements results in scar resorption.

The very first event which usually occurs in a wound is blood extravagation, that results in platelet aggregation and impregnation of the wound with platelet and serum constituents. Among these constituents are polypeptide growth factors, which are known to play a major role in tissue regeneration. Platelet a granules, which are released by aggregated platelets, are one of the richest physiological source of platelet-derived growth factor (PDGF) and transforming growth factor β (TGFβ), while serum contains high amounts of insulin-like growth factor I (IGF-I), IGF-II and their binding proteins (IGF-BPs) (Strovbant P & Waterfield M. D., *Endo. J.*, 1984, 2:2963–2967; Assoian R. K. et al., *J. Biol. Chem.*, 1983, 258:7155–7160: Sara V. R. et al., *Physiol. Rev.*, 1990, 70:591–614).

PDGFs include PDGF, platelet derived angiogenesis factor (PDAF), TGFβ and platelet-factor-4 (PF-4), which is a chemoattractant for neutrophils (Knighton et al., In *Growth Factors and Other Aspects of Wound Healing Biological and Clinical Implications*, Alan R. Liss, Inc., pp. 319–329 (1988)). PDGF is a mitogen and chemoattractant for fibroblasts and smooth muscle cells and is a stimulator of protein synthesis in cells of mesenchymal origin, including fibroblasts and smooth muscle cells. PDGF is also a nonmitogenic chemoattractatt for endothelial cells.

TGFβ is a chemoattractant for macrophages and monocytes. Depending upon the presence or absence of other growth factors, TGFβ increases the tensile strength of healing dermal wounds. TGFβ also inhibits endothelial cell mitosis, and stimulates collagen and glycosaminoglycan synthesis by fibroblasts.

Other growth factors, such as EGF, TGFα, the HBGFs and osteogenin, are also important in wound healing. EGF, which is found in gastric secretions and saliva, and TGFα, which is made by both normal and transformed cells, are structurally related and may recognize the same receptors, which mediate cell proliferation on epithelial cells Both factors accelerate re-epithelialization of skin wounds.

The in vitro mode of action of these growth factors involves chemoattraction at the wound site, call proliferation and collagen synthesis. One very-interesting feature of these products is that some of them, namely PDGF and IGFs, work synergistically in stimulating wound repair (Lynch S. E. et al., *J. Clin. Invest.*, 1989, 84:640–646, Greenhalgh D. G. et al., *Wound. Rep. Reg.*, 1993, 1:54–62).

Growth factors are, therefore, potentially useful for specifically promoting wound healing and tissue repair. The addition of exogenous growth factors to a wound has been shown to increase the rate at which the wound is closed, the number of cells in the healing area, the growth of blood vessels, the total rate of deposition of collagen, and strength of the scar (Carter et al., in *Growth Factors and Other Aspects of Wound Healing: Biological and Clinical Implications*, Alan R. Liss, Inc., pp. 303–317 (1988)).

Platelet-derived wound healing formula (PDWHF), a platelet extract which is in the form of a salve or ointment for topical application, has been described by Knighton et al. (*Ann. Surg.*, 1986, 204: 322–330). Knighton et al. (*Ann. Surg.*, 1986, 204: 322–330 & In *Growth Factors and Other Aspects of Wound Healing: Biological and Clinical Implications*, Alan R. Liss, Inc., pp. 319–329 (1988)) describe a process for the preparation of a platelet-derived wound healing composition by centrifuging platelets and treating them with thrombin to stimulate the production of a releasate, which can be combined with collagen. Knighton et al. obtain a platelet-derived releasate having a limited Concentration of growth factors with high concentration of albumin (9.9%), which limits its clinical uses. Also, this platelet-derived releasate contains essentially non-mature growth factors due to the use of thrombin to break apart the platelets and release their content.

Clinical evaluation of recombinant growth factors are underway but it remains so far uncertain whether the therapeutic benefit of these drugs will pay for their high cost of production specially if used in combination.

Autologous human platelet derived wound healing formula, made of thrombin activated platelet a granules, has also been shown to induce the healing of chronic ulcers, thus indicating that growth factor extracts may constitute an advantageous alternative to the use of recombinant growth factors if proven to be economically extractable.

It would be highly desirable to be provided with a economical and easy to carry out process for the isolation of contamination-free blood derived platelet extract for use in a wound dressing composition. Such a blood derived platelet extract should be absolutely free of Hepatitis B and HIV contaminants.

It would be highly desirable to be provided with a process for the isolation of platelet extract containing matured growth factors with minimal albumin concentration (0.4%) and improved contents of wound healing substances (growth factors, fibronectin, thrombospondin, etc.), which would be derived from whole porcine blood, and suitable for use in a wound dressing composition.

It would be highly desirable to be provided with a method for the promotion of wound healing of a patient which comprises the topical administration of the pharmaceutical composition on the wound of the patient.

SUMMARY OF THE INVENTION

One aim of the present invention is to provide a process for the isolation of platelet extract containing matured growth factors at a concentration such that it contains minimal albumin and optimal growth factors, fibronectin and thrombospondin.

Another aim of the present invention is to provide for a process which results in an improved platelet extract containing matured growth factors and only traces of albumin.

In accordance with one embodiment of the present invention, there is provided a process for the preparation of porcine platelet-extract containing matured growth factors, which comprises the steps of:

a) centrifuging whole porcine blood at about 1000 g to about 5000 g to isolate the platelets from the platelet-rich-plasma;

b) resuspending the isolated platelets of step a) in Plasma-Lyte A and centrifuging to concentrate the platelets;

c) washing the concentrated platelets of step b);

d) lyophilizing the washed platelets of step c); whereby causing lysis of the platelets and producing the platelet extract.

In accordance with another embodiment of the present invention, the process further includes a step of resuspension in pure water after step d), wherein the lyophilized platelets are resuspended.

In accordance with another embodiment of the present invention, there is provided a pharmaceutical composition for promoting wound healing, which contains an effective concentration of a platelet extract prepared according to the process of the present inventions wherein the platelet extract contains matured growth factors, thrombospondin, fibronectin and minimal albumin; in association with a pharmaceutically acceptable carrier. Such a pharmaceutical composition has a platelet extract concentration between $10^7$ to $10^{12}$ platelet equivalent/ml with only traces of albumin proteins.

In accordance with another embodiment of the present invention, there is provided a method for the promotion of wound healing of a patient which comprises the topical administration of the pharmaceutical composition on the wound of the patient.

For the purpose of the present invention the following terms and abbreviations are defined below.

"PRP" is intended to mean & platelet-rich-plasma, preferably of porcine origin prepared by low speed centrifugation in order to pellet, and remove erythrocytes and leukocytes.

"PE" is intended to mean a platelet extract.

"PPP" is intended to mean a platelet-poor-plasma.

DETAILED DESCRIPTION OF THE INVENTION

Figure 1A:
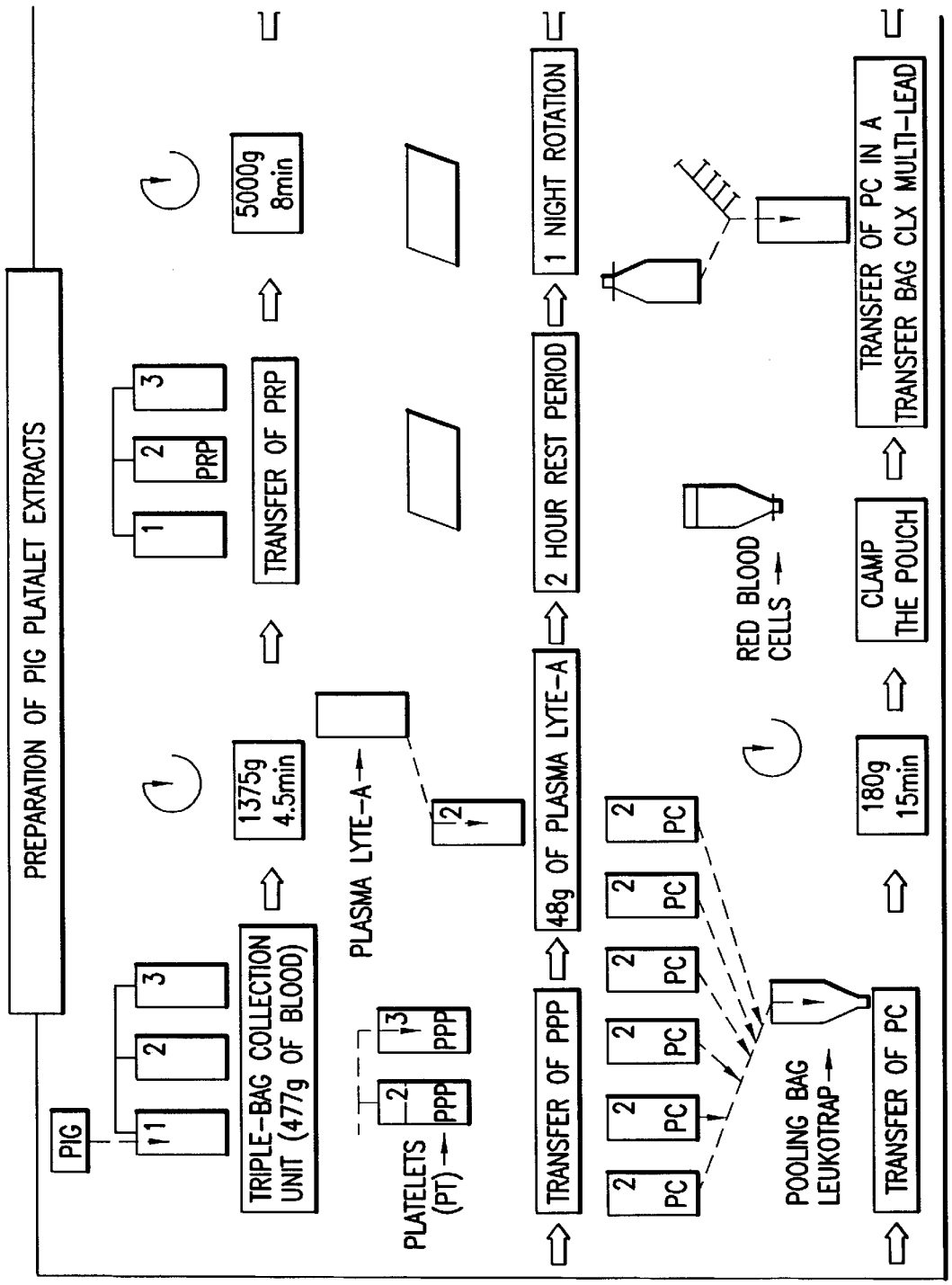
FIG. 1 illustrates the preparation of porcine platelet extracts in accordance with one embodiment of the present invention.

The process of the present invention for the manufacture of porcine platelet extracts is new, simple and inexpensive. Moreover, the porcine origin of the blood, in accordance with the present invention, guaranties: 1) a total absence of potential transmission of human viral agents (Hepatitis, HIV, etc.); 2) the production of growth factors nearly 100% identical to their human counterparts and, 3) a reliable, largely available and highly reproducible source of raw material.

The process of the present invention results in an improved platelet extract containing matured growth factors and only traces of albumin.

The preferred embodiments of the process of the present invention are more specifically described as follows, which is intended to illustrate the invention rather than to limit its scope.

1. Blood Extracts Preparation 1.1 Blood Collection

For experimental purposes, porcine whole blood was used in accordance with the present invention due to its availability and its contamination-free characteristic. Thus, young Landrace, Yorkshire, male castrated 2 month-old piglets of 25 kg B.W. were purchased from a local breeder). They were housed for 2–5 days in our facilities with free access to water and food. For blood collection, they were anaesthetized with ketamine hydrochloride (10 mg/kg BW), then with fluothane by intratracheal administration. A cannula was aseptically inserted into one carotid artery. Before animals were exsanguinated, 2 ml of heparin saline was injected in the cannula system and the same volume was vacuumed out. About 450 ml of sterile blood was collected in each triple bag (CLX CPDA-1, sold by Miles Canada).

1.2 Platelet-rich-plasma (PRP)

The collected sterile whole porcine blood was centrifuged in its collection bag for about 4.5 min. at 1375 g (BRAKE= 3; Rotor JS-4.2; Beckman™ J6-B). The supernatant, platelet-rich-plasma (PRP), was collected by emptying the content of the centrifuged bag in a second bag until the red blood cells are at about 1 cm of the top edge of the emptied bag.

1.3 Platelet Concentrate (PC)

The collected platelet-rich-plasma (PRP) was immediately centrifuged in its storage bag for about 8 min. at 5000 g (BRAKE=maximum; Rotor JS-4.2; Beckman™ J6-B). After centrifugation, the platelet-poor-plasma (PPP) was transferred to a third bag until maximum removal of the PPP or when a volume of about 10 ml remains in the second bag containing the platelet concentrate. The PPP was discarded.

The second bag containing the platelet concentrate was resting on a weigh-bridge (Sartorius™ LC-4800-P). A bag of Plasma-Lyte A™ (Baxter) was connected to a secondary medication device, followed by a septum and a needle of 18G ×1½. The needle was introduced through a membrane located in one of the bag's chimney 48 g of Plasma-Lyte A™ was injected into the bag.

The platelet concentrate was left to rest for 2 hours and was then agitated overnight on a horizontal shaker (New Brunswick Scientific, model G20) at 25 RPM and 22° C.

1.4 Washing of the Platelet Concentrate (PC)

The content of six (6) platelet concentrate bags were collected in a six-line Leukotrap™ bag (Miles Canada). Centrifuged for 15 min. at 180 g (BRAKE=maximum; Rotor JS-4.2; Beckman™ J6-B). The appendix of the bag containing the red blood cells residue was closed using the clamp which is usually used for retaining leukocytes. The bag was turned upside down, suspended and the supernatant was transferred in a six-line CLX bag (Miles Canada) using the proximal line. The order of the lines used is always from the proximal to the distal.

Centrifuged for 8 min. at 5000 g (BRAKE=maximum; Rotor JS-4.2; Beckman™ J6-B). The bag was placed on a plasma press (Miles Canada) and the maximum of supernatant was removed in a beaker. The line was closed using an aluminum ring.

The bag containing the centrifuged platelet concentrate was placed on a weigh-bridge (Sartorius™ LC-4800-P) and was injected with 48 g of Plasma-Lyte A™ using one line of the CLX bag. The bag opening was temporarily blocked using a hemostatic claw or an aluminum ring to prevent a relux in the lines.

The platelet concentrate was left to rest for one hour and was then agitated for about one hour or until complete resuspension on a horizontal shaker (New Brunswick Scientific, model G20) at 25 RPM and 22° C.

The bag was placed on a weigh-bridge (Sartorius™ LC-4800-P) and was injected with 360 g of Plasma-Lyte A™ using one line of the CLX bag. Mixed well.

The content of the bag was transferred to a graduated cylinder for the cellular culture. The volume was measured. 1 ml is taken to at 5 ml polypropylene tube in a sterile manner. The platelets, red blood cells and white blood cells are counted. The total quantity of platelets obtained was calculated along with a mean per bag of blood collected. For five extractions, a mean value of $57 \pm 13 \times 10^9$ platelets/bags was obtained.

The platelet concentrate was then transferred in sterile conical tubes of 250 ml. These were centrifuged without the cover of the rotor for 20 min. at 2900 g (BRAXE= maximum; Rotor JS-4.2; Beckman™ J6-B).

1.5 Platelets Extract (FE) Preparation

The platelet residue was removed from the supernatant and was resuspended at $1 \times 10^{10}$ platelets/ml in picopure water at 4°C. This was frozen in thin layers using liquid nitrogen, and then lyophilized.

The lyophilized platelets were resuspended in sterile picopure water at 4° C.

These were centrifuged in Oak Ridge tubes for 30 min. at 40 000 g and 4° C. (BRAKE=maximum; Rotor JA-20; Beckman™ J2-21).

Aliquoted in 1, 2 or 5 ml and stored at −80° C.

2. Analytical Procedures

Proteins were measured by a Lowry method (*J. Biol. Chem.*, 1951, 193:265–275) using a commercial kit sold by Sigma Chemical (St. Louis, Mo.).

Platelet-derived growth factor (PDGF) was measured by radioimmunoassay using a commercial kit (Amersham International, UK) according to the following procedure.

| PORCINE PDGF RIA PROCEDURE | | | | |
|---|---|---|---|---|
| Tube # | Standard or sample | Buffer | $I^{125}$-PDGF-2 $\beta\beta$ | $Ab_1$ Raised in goat |
| 1- Trace | — | — | 100 μl | — |
| 2- Background | — | 400 μl | 100 μl | — |
| 3- Zero | — | 300 μl | 100 μl | 100 μl |
| 4- 0.044 ng/tube | 100 μl | 200 μl | 100 μl | 100 μl |
| 5- 0.137 ng/tube | 100 μl | 200 μl | 100 μl | 100 μl |
| 6- 0.410 ng/tube | 100 μl | 200 μl | 100 μl | 100 μl |
| 7- 1.230 ng/tube | 100 μl | 200 μl | 100 μl | 100 μl |
| 8- 3.700 ng/tube | 100 μl | 200 μl | 100 μl | 100 μl |
| 9- 11.000 ng/tube | 100 μl | 200 μl | 100 μl | 100 μl |
| 10- 33.000 ng/tube | 100 μl | 200 μl | 100 μl | 100 μl |
| 11- 100.000 ng/tube | 100 μl | 200 μl | 100 μl | 100 μl |
| 12- unknown ng/tube | 100 μl | 200 μl | 100 μl | 100 μl |

Incubation: 20 to 24 hours at 22° C.
Precipitation: 2nd antibody precipitation (100 μl) 50 μl 4% normal goat plasma and 50 μl donkey anti-goat gamma globulins (diluted 1 in 5 with buffer), vortex, leave 18 hrs or overnight at 22° C., centrifuge 35 mins at 3200 rpm, decant and count
Dilution of standard: Porcine PDGF 1 ng/ml frozen in aliquot of 500 ml (500 ng/500 μl)
1. 200 μl is added to 400 μl buffer = 33.3 ng/100 μl;
2. A serial dilution is made by 1/3 for standard from 100 ng/100 μl to 0.044 ng/100 μl.
Dilution of $Ab_1$ (anti-hPDGF-BB, AB-220-NA):
1. Frozen in 40 μl aliquots of a dilution of 1/1;
2. 20 μl in 1980 ml of buffer make a dilution of 1/100. Take 100 μl of 1/100 $Ab_1$ in 16 μl buffer, make a final dilution of 1/80K.
Tracer: $^{125}$I-PDGF$_1$ (Dupont) diluted in PDGF buffer so that 100 μl = 13000 cpm.

According to the manufacturer's data, cross reactivity of porcine PDGF is 38% with the anti human PDGF antibody used in the kit. Results were therefore converted in porcine PDGF equivalent by dividing then by 0.38.

Transforming growth factor β1 and β2 were measured using the Quantikine test™ commercially available (R and D Systems, Minn., U.S.A.). Before measurement, extracts were mixed 1:2 either in distilled water or in trifluoroacetic acid (TFA) 1%, incubated for 1 hour at room temperature, lyophilized and reconstituted with water to their initial volume. This procedure was conducted in order to determine if TGFβ was present in extracts as an active or latent, high molecular weight form.

3. In Vitro Assays 3.1 Pig Anaesthesia

A pig of 25 kg±2 kg was injected intramuscularly with ketamine (15 mg/kg). After 5 to 10 min., the pig was tracheotomized, intubated and artificially ventilated using a mechanical respirator. The current volume was fixed at 15 cc/kg and the respiratory frequency was maintained between 10 and 15 per min. to keep a Pa $CO_2$ between 35 and 45 mmHg. The anaesthesia was asserted with 1.5% to 2.0% fluothane.

3.2 Skin Removal

The pig was placed in a decubitus position, the skin sections were removed from the postero-anterior region. This region was previously shaved, washed with compresses impregnated with cidex, rinsed with tap water and then abundantly sprayed with 70% ethanol.

Skin strips of 15 cm by 2.5 cm were removed using a sterile scalpel blade. The strips were bathed successively in 50 ml sterile tubes containing 40 ml 70% ethanol, then in sterile PBS (phosphate buffer saline) and finally in a sterile washing culture (DMEM, 5% penicillin-streptomycin, 125 ug/ml fongizone).

3.3 Digestion Method

Under the flux hood, the strips are immediately transferred in a sterile petri of 145 cm² containing 100 ml of washing culture medium. Each strips is cut in pieces of 2.5 cm by 2.0 cm using a scalpel blade and a sterile tissue tongs.

Pieces of tissue were then incubated in a washing medium for 60 min. at room temperature under the flux hood in order to sterilized the pieces in the culture medium containing antibiotics. The pieces were then washed in three successive baths of 100 ml of sterile PBS in petri dishes.

In a digestion bottle of 250 ml having a magnetic agitator, pieces of tissue were digested under agitation in 100 ml of pronase at a concentration of 1 mg/ml in DMEM, 1% penicillin-streptomycin in an incubator under 5% $CO_2$ atmosphere at 37° C. for one hour.

After a one-hour digestions the pronase enzyme was decanted and the tissue pieces were washed with washing medium. To complete the digestion, the tissue pieces were put back under agitation during 18 hours in 100 ml of collagenase IV at a concentration of 300 $\mu$/ml in a DMEM medium, 1% penicillin-streptomycin.

3.4 Cell Culture

After an 18-hour incubation, the cell suspension was then centrifuged in sterile tubes (50 ml) for 5 min. at 800 g in a table centrifuge. The supernatant was decanted and the cell residue was resuspended in a DMEM medium. A 50 ul cell aliquot was mixed well with 10 ml of ISOTON II™, (Sodium chloride 7.93 g/l, Disodium EDTA 0.38 g/l, Potassium chloride 0.40 g/l, Monosodium phosphate 0.19 g/l, Sodium fluoride 0.30 g/l; sold by Coulter) in a counting cupule. From this mix a 500 ul volume is counted using a Coulter Counter ZM™ (Coulter Electronics of Canada Ltd.) which the counting bounds were previously fixed. The cells were then inseminated to a density of $50 \times 10^6$ in 175 $cm^2$ bottles containing 25 ml of DMEM, 10% CFS (Calf Fetal Serum), 1% penicillin-streptomycin and were placed in an incubator at 37° C., 5% $CO_2$ and 100% humidity. When most of the cells have adhered, about 4 hours after the insemination, the culture medium is then replaced, and also the following day. The cell adhesion was estimated at about 30%. The cells were then trypsinized each 2 days according to a dilution of ¼ of the cell residue per bottle.

3.5 Biological Assays on Porcine Culture Fibroblasts

The effect of the samples was systematically verified on the growth and the metabolism of porcine fibroblasts. This assay allows to detect if samples act upon the proliferation and the metabolism of cells (inhibition, stimulation or lethal effect). The samples effect was always compared to the effect of foetal veal serum of a concentration of 10% (positive control).

Experimental Protocol of Proliferation Assay

Day 1: The assay was effected with Fibroblasts at passage 4. Thus, the fibroblasts which have come to passage 3 were dispersed during 3 to 4 min. with 10 ml of trypsin—EDTA, which was added with 15 mM of a HEPES solution to adjust the pH to 7.4. When the cells were completely detached, the dispersion was stopped with 1 ml CFS and those were centrifuged 5 min. at 800 g in a table centrifuge. The residue was resuspended in DMEM, a 50 ul aliquot of cells was mixed well with 10 ml of Isoton II™ contained in a counting cupule. From this mix a 500 ul volume is counted using a Coulter Counter ZM™ which the counting bounds have been set previously. The cells were inseminated to a density corresponding to 80000 cells/ml of DMEM, 10% CPS, 1% penicillin-streptomycin.

Under agitation using a magnetic bar contained in a sterile bottle, 1 ml of medium containing the cells were added to each well of a 12-well plate using a repetition pipette and a 50 ml sterile conical tube. The plates were incubated at 37° C., 5% $CO_2$ and 100% humidity during 18 hours in an incubator.

Day 0. After having adhered, the cells are washed with DMEM medium heated at 37° C. The medium was then withdrawn by vacuuming. Then, 1 ml of washing medium was added to each well with a serological polystyrene pipette of 10 ml and withdrawn again by vacuuming. To each well, 900 ul of experimental medium containing DMEM, 0.5% CFS and 1% of penicillin-streptomycin was precisely added with an automatic pipette of 100 ul. Furthermore 100 ul of a sample concentrated 10× was added using an automatic pipette of 100 ul. Each plate included 3 samples and 1 negative control (basal level) effected in triplicate. For each sample, a serial dilution was executed in the experimental medium in sterile tubes of 3 ml as follows.

| For 80 ul/ml final: | 1) 800 ul sample + 200 ul experimental medium |
|---|---|
| 40 ul/ml final: | 2) 500 ul solution 1) + 500 ul experimental medium |
| 20 ul/ml final: | 3) 500 ul solution 2) + 500 ul experimental medium |
| Control: | DMEM + 0.5% CFS + 1% penicillin-streptomycin |

Also, a positive control of 100 ul CFS was added to the medium contained in the wells, as well as a stimulation control of a sample standard, were effected to verify the assay.

In order to see the progression of cellular proliferation, wells of positive and negative controls were effected on day 0 and day 1. The cellular dispersion method is described for day 2 below.

Day 2: The dispersion of cells was also effected with trypsin-EDTA previously equilibrated for 18 hours at 37° C. under 5% $CO_2$. The medium was withdrawn by vacuuming, then the cells were washed with 1 ml of DMEM medium heated at 37° C. After having vacuumed the washing medium, 1 ml of trypsin maintained at 37° C. is added in the wells. The cells detachment was observed with a microscope. When the cells were completely loose, the dispersion was stopped by adding 100 ul of CFS.

The cells were suspended by three successive reversal with a glass serological pipette of 5 ml. The suspension was transferred, by carefully taken each bubbles, in 7 ml of Isoton II™ contained in a counting cupule. The well was then rinsed by three: successive reversal with 2 ml Isoton II™ and added to the previous 7 ml. Before counting, the Isoton II™ containing the cells was mixed well 5 times, with a serological polystyrene pipette of 10 ml, in the cupules. A 500 ul volume of the mix was counted using a Coulter Counter™ with the counting bounds previously set.

Experimental Protocol of the Measurement of the Metabolic Activity

Day 1: The assay was effected with Fibroblasts at passage 4. Thus, the fibroblasts which have come to passage 3 were dispersed during 3 to 4 min. with 10 ml of trypsin-EDTA, which was added with 15 mM of a HEPES solution to adjust the pH to 7.4. When the cells were completely detached, the dispersion was stopped with 1 ml CFS and those were centrifuged 5 min. at 800 g in a table centrifuge. The residue was resuspended in DMEM, a 50 ul aliquot of cells was mixed well with 10 ml of Isoton II™ contained in a counting cupule. From this mix, a 500 ul volume is counted using a Coulter Counter ZM™ which counting bounds which have been set previously. The cells were inseminated to a density corresponding to 8500 cells/200 ul of DMEM, 10% CFS, 1% penicillin-streptomycin.

Under agitation using a magnetic bar contained in a sterile bottle, 200 ul of medium containing the cells were added to each well of a 96-well plate using a multichannel pipette, while leaving the outside wells empty and the penultimate row free for the reaction blank. The plates were incubated at 37° C., 5% $CO_2$ and 100% humidity during 18 hours in an incubator.

Day 0: After having adhered, the cells are washed with DMEM medium heated at 37° C. The medium was then withdrawn by vacuuming. Then, 1 ml of washing medium was added to each well and withdrawn again by vacuuming. To each well, 90 ul of experimental medium containing DMEM, 0.5% CFS and 1% of penicillin-strep tomycin was precisely added with a multichannel pipette. Furthermore 10 ul of a sample concentrated 10× was added using an automatic pipette of 10 ul. Each plate included 5 samples of 3 dosages, 1 negative control (basal level) and 1 positive control (10 ul of CFS was added to each 90 ul medium present in each well. These were all effected in triplicate. Within the samples, a stimulation control of a standard sample is effected in order to verify the validity of the assay. For each sample, a serial dilution was executed in the experimental medium in sterile tubes of 3 ml as follows.

| For 80 ul/ml final: | 1) 800 ul sample + 200 ul experimental medium |
|---|---|
| 40 ul/ml final: | 2) 500 ul solution 1) + 500 ul experimental medium |
| 20 ul/ml final: | 3) 500 ul solution 2) + 500 ul experimental medium |
| Control: | DMEM + 0.5% CFS + 1% penicillin-streptomycin |

In order to see the progression of cellular proliferation, wells of positive and negative controls ware effected on day 0 and day 1. The method of treatment is described for day 2 below.

Day 2: After a two-day incubation, 25 ul of MTT reactant (5 mg/ml concentration) was added to 100 ul medium in each well. This must be effected without any light. The plates are then return to incubate in the dark at 37° C. for at least two hours. Then, 100 ul of lysing buffer were added to each well, and left to incubate for 18 hours in the dark at 37° C. The next day, the 96-well plates were read using a ELISA spectrophotometer at a wavelength of 470 nm and having previously determined the reaction blank pattern.

Preparation of MTT Reactant
Concentration: 5 mg/ml (for 100 ml weight 500 mg) 500 mg MTT/100 ml PBS filtered on 0.22 mm
Store at 4° C. in a brown bottle away from the light. Can be store up to one month.
Lysing Buffer
For 200 ml prepare:
50% DMF=105 ml DMF+105 ml $H_2O$
20% SDS=40 g SDS+180 ml DMF 50%

The pH was adjusted at 4.7 with acetic acid (80%) 2.5% HCl (5 ml HCl 1N+5 ml acetic acid 80%). Completed to 200 ml with DMF 50%.

Platelets α granules are the richest in vivo source of TGFβ and PDGF. Porcine platelets contain two isotypes, TGFβ 1 and β 2. Human and porcine TGFβ 1 have total sequence identity and TGFβ 2 has approximately 70% homology with TGFβ 1. All TGFβs are naturally found as a latent, high molecular weight, inactive complexes in platelets. In the platelet extracts of the present invention, the measurement of non-extracted and acid-extracted platelet extracts yielded the same amount of TGFβ 1 and β 2, indicating that TGFβ 1 and β2 are present in our extracts in its active form of about 25 KD.

PDGF is a disulfide-linked dimer with a molecular weight 30–32 KD. The subunits of the dimer are two related polypeptides designated the A and B chains. Although human platelet PDGF has been shown to consist of PDGF-AB and PDGF-BB, porcine platelet PDGF consists primarily of PDGF-BB homodimers. Because of its higher affinity for the type B PDGF receptor, PDGF-BB is more potent than PDGF-AB in stimulating cell proliferation in vitro. However, in vivo data suggest that PDGF AB and BB have equal potency as wound healing enhancers.

Both PDGF and TGFβs are known as stimulators of wound healing. They both induce extracellular matrix synthesis, granulation tissue formation and increase wound breaking strength in a variety of animal models. Both recombinant TGFβ 1 and β2 and PDGF-BB are currently tested in clinical trials as therapeutic agents for the healing of chronic ulcers with promising initial results.

In addition to PDGF and TGFβ, platelet α granules have been shown to contain a number of agents that might play a role in the process of wound healing. Among these substances are Platelet Factor 4 (PF4), a platelet-derived Endothelial Cell Growth Factor (pdECGF), an Epidermal Growth Factor-like protein (EGF), and traces of IGF-I, IGF-II and IGFBP3.

Thus, the, analytical results showed that the process of, extraction in accordance with the present invention successfully recovered PDGF and TGFβ from platelets.

In cell culture, the platelet extracts of the present invention stimulated fibroblast proliferation in a dose dependent manner. PE induced a dose-dependent increase of porcine primary cultured fibroblasts (PPCF).

Recently, a randomized, double blind and placebo clinical study reported significant improvements in diabetic ulcers treated with an homologous human platelet lysate derived from pooled human platelets. Moreover, a cost-efficacy analysis conducted for this study revealed that, the treatment was associated with a 38% decrease in the medical costs when compared to a conventional therapy. Although the composition of the PE of the present invention differs from that of the human platelet lysate (thrombin activated platelet wound healing formula) developed by Curative Technologies Inc., the results of this study illustrate the therapeutic potential and the advantages of growth factor extracts over recombinant growth factors.

The present invention will be more readily understood by referring to the following examples which are given to illustrate the invention rather than to limit its scope.

EXAMPLE I

Figure 1B:
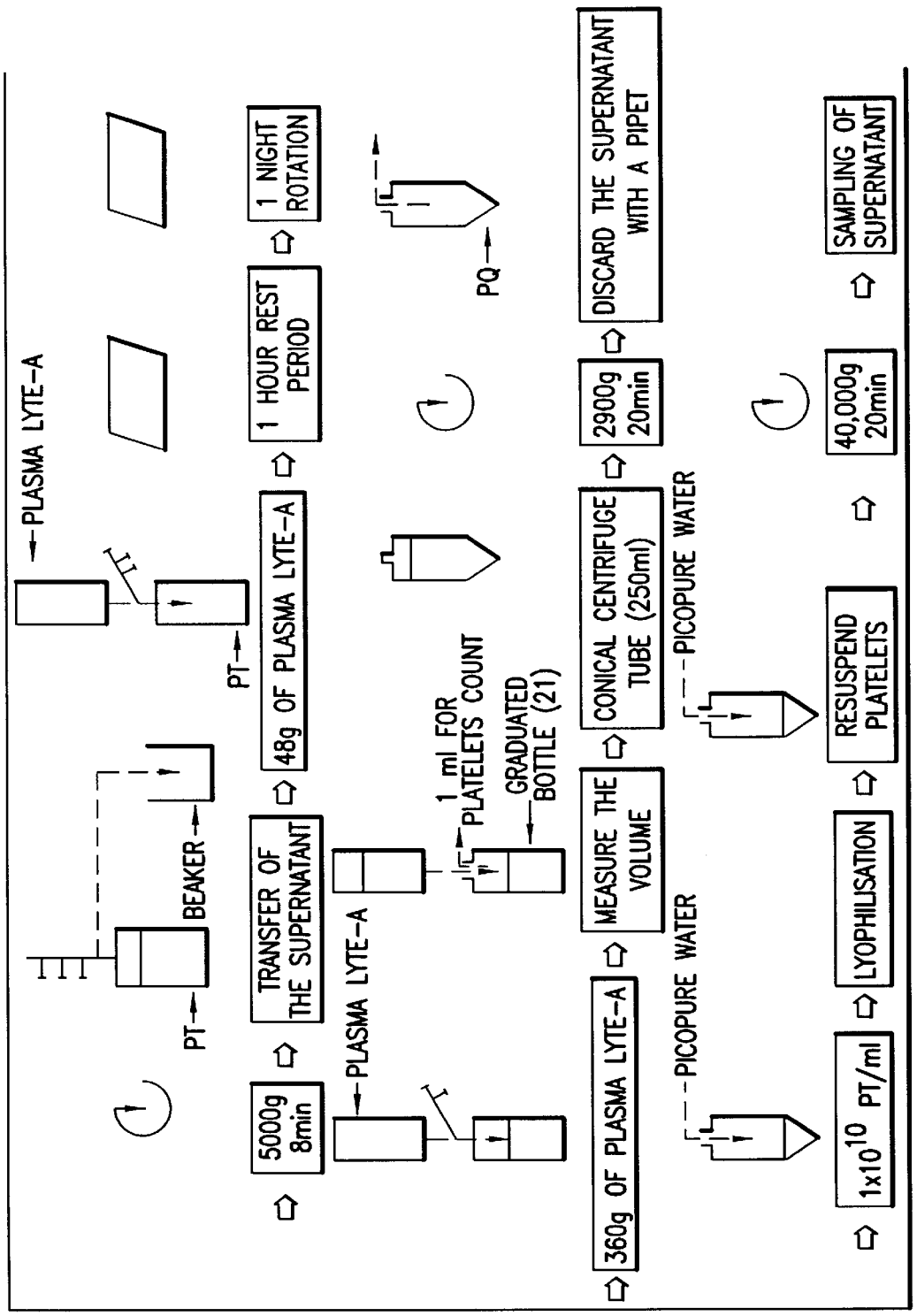

Porcine Platelet Extracts Prepared in Accordance with the Present Invention as Compared to the Extracts of the Knighton Procedure Porcine-platelet Extracts of the Present Invention The platelet extracts were prepared according to the procedure described above and as illustrated in FIG. 1, but with the following distinctions.

Extracts: EP-95-11

The platelet residue was removed from the supernatant and was resuspended at $1\times10^{10}$ platelets/ml in picopure water at 4° C. This was frozen in thin layers using liquid nitrogen, and then lyophilized.

Extract: EP-PL-LYTE

The platelet residue was removed from the supernatant and was resuspended at $1 \times 10^{10}$ platelets/ml in PLASMA-LYTE™, (an electrolyte solution, pH 7.4, sold by Baxter) at 4° C. This was frozen in thin layers using liquid nitrogen, and then lyophilized.

Knighton Porcine Platelet Extracts

Figure 2A:
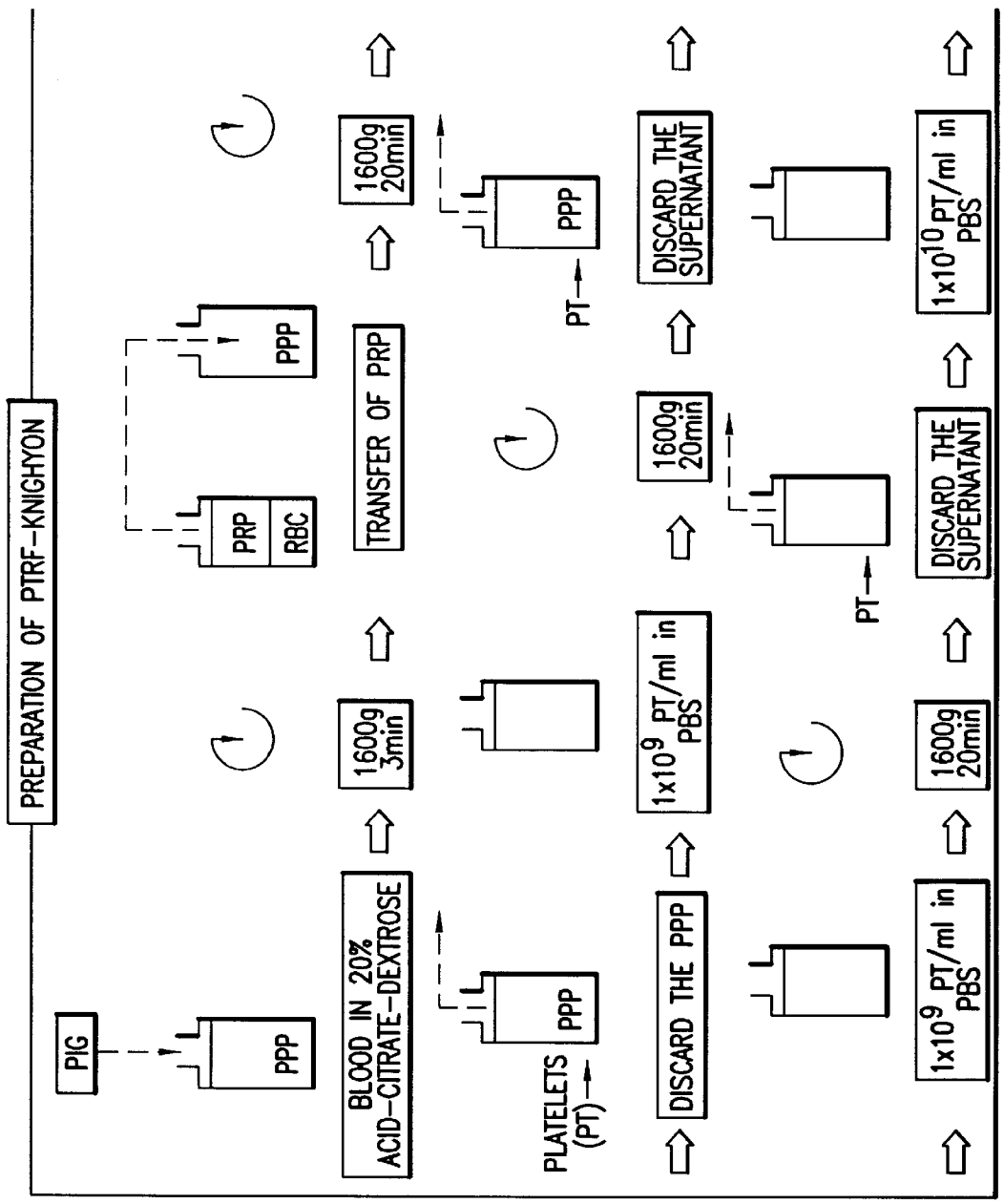
FIG. 2 illustrates the preparation of platelet reference (PTRF) according to the procedure of Knighton.
Figure 2B:
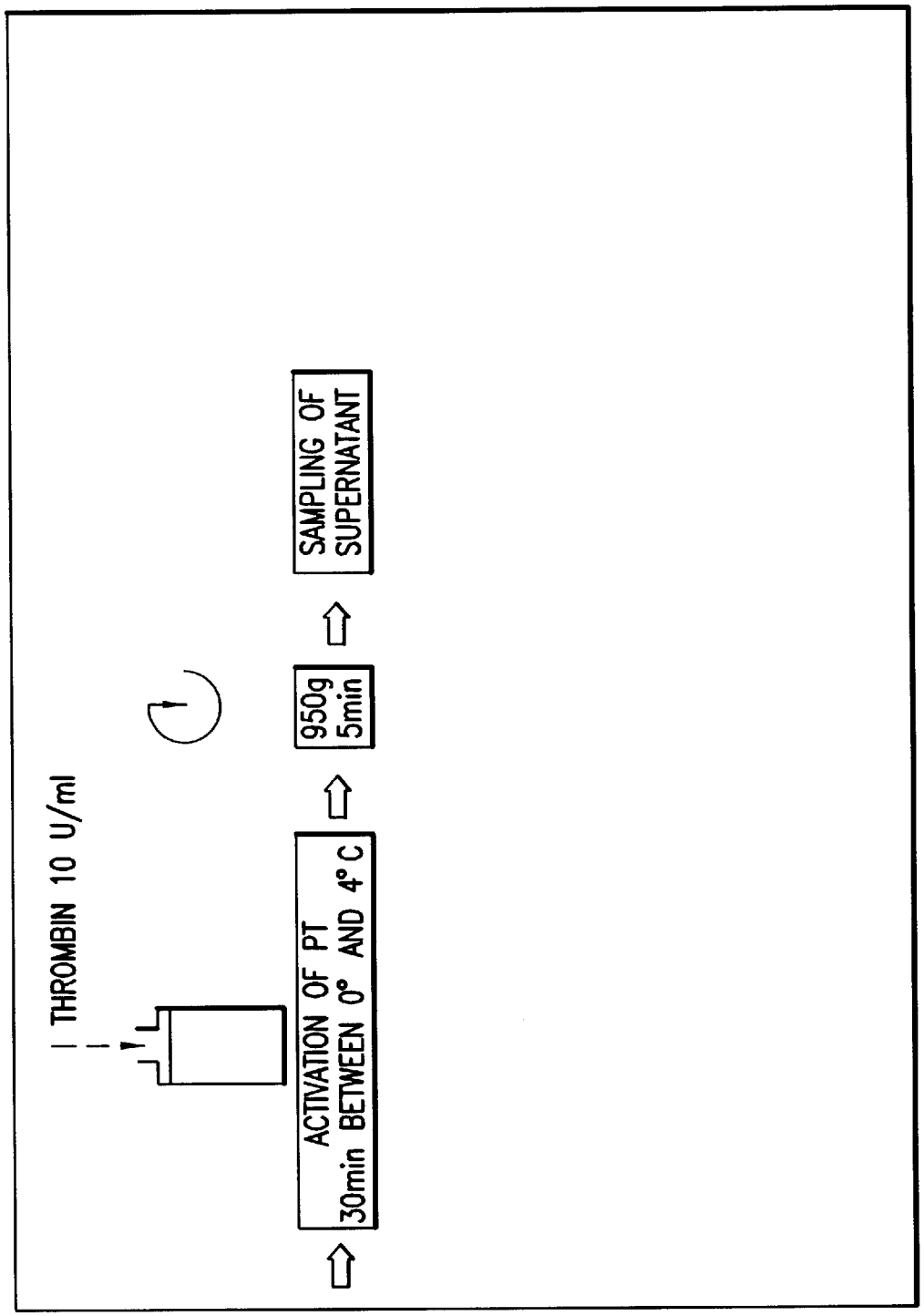

The platelet extracts of Knighton, as illustrated in FIG. 2, were used to serve as a comparison with the platelet extracts of the present invention. The Knighton procedure is a known method published by Knighton et al. (*Ann. Surg.*, 1986, 204: 322–330).

A. Pig Preparation

A pig of 20–28 kg was injected intramuscularly in its hindside region with 4–5 ml Ketaset™. After 5 to 10 min., the pig was weighed and anaesthetized with fluothane. The pig was placed on its back with its legs attached to the anesthetic table. Then, the tracheotomy was made and the tracheal tube was introduced in the trachea and the balloon was inflated. The pig was connected to the mechanical respirator. The carotid was cleared. A catheter was introduced in the carotid, which was connected to a two-way faucet and to a septum. Before animals were exsanguinated, about 2 ml of heparin saline was injected in the cannula system and the same volume was vacuumed out.

B. Blood Collection

Blood was collected using a 60 ml syringe containing 12 ml of acid-citrate-dextrose buffer.

C. Platelet-rich-plasma Preparation

The collected sterile whole porcine blood was centrifuged in 450 ml bottles for about 3 min. at 1600 g and 22° C. (BRAKE=maximum; Beckman™ J2-21). The supernatant, platelet-rich-plasma (PRP), was transferred in 450 ml bottles.

D. Preparation of the Platelet Concentrate

The collected platelet-rich-plasma (PRP) was immediately centrifuged for about 20 min. at 1600 g and 22° C. (BRAKE=6; Beckman™ J2-21). The platelet-poor-plasma (PPP) was discarded.

E. Washing of the Platelet Concentrate

The red blood cells residue was resuspended in PBS buffer (pH 7.4) to obtain a platelet concentration of $10^9$ platelets/ml. Centrifuged in 450 ml bottles for about 20 min. at 1600 g and 22° C. (BRAKE=6; Beckman™ J2-21).

The residue was resuspended in PBS buffer (pH 7.4) to obtain a platelet concentration of $1 \times 10^{10}$ platelets/ml.

F. Method of Activation of the Platelets

10 µg/ml of thrombin was added to the platelets and incubated for 30 min. between 0° C. and 4° C. The platelets were centrifuged in 450 ml bottles for about 5 min. at 950 g and 4° C. (BRAKE-6; Beckman™ J2-21).

The supernatant containing the granules is aliquoted in 2 ml tubes and stored at –80° C.

TABLE 1

Comparative evaluation of porcine platelet extracts

| Extracts | Porcine Weight (kg) | Proteins mg/ml | Albumin ug/ml | Alb/Prot % | TGF-β1 ng/ml | PDGF ng/ml | Thbs ug/ml | FbN ug/ml |
|---|---|---|---|---|---|---|---|---|
| PTRF (Knighton) | 26 | 1.9 | 188 | 9.9 | 151 | 81 | 2.9 | 5.6 |
| EP-95-11 | 37 | 6.6 | 40 | 0.6 | 169 | 171 | 10.2 | 13.1 |
| EP-PL-LYTE | 27.5 | 9.2 | 36.9 | 0.4 | 217 | 269 | 17.4 | 20.1 |

It can be seen in Table 1 that the platelet extract EP-95-11 produced by the process of the present invention, which consists in resuspension in pure water before a final step of lyophilisation and further resuspension in pico pure water, resulted in an increased concentration of PDGF, TGF-β1, thrombospondin (Thbs), and fibronectin (FbN) as compared to the Knighton extract (PTRF). But, most importantly, the platelet extract EP-95-11 contains only traces of albumin with respect to its protein content when compared with the PTRF of Knighton.

Furthermore, the platelet extract EP-PL-LYTE produced by the process of the present invention, which consists in resuspension in Plasma-Lyte™ before a final step of lyophilisation, in order to further preserve the integrity of the platelets, and resuspend in pico pure water, resulted in an even more increased concentration of PDGF, TGF-β1, thrombospondin (Thbs), and fibronectin (FbN) as compared to the Knighton extract (PTRF). But, most importantly, the platelet extract EP-95-11 contains even lower traces of albumin with respect to its protein content as compared to the PTRF of Knighton and even the platelet extract EP-95-11.

TABLE 2

In vitro bioactivity of porcine platelet extracts on primary culture fibroblasts

| Extracts | Porcine Weight kg | Proliferation (%)/Control | | | MTT (%)/Control | | |
|---|---|---|---|---|---|---|---|
| | | 20 ul | 40 ul | 80 ul | 20 ul | 40 ul | 80 ul |
| PTRF (Knighton) | 26 | 134 | 146 | 205 | 187 | 206 | 209 |
| EP-95-11 | 37 | 153 | 234 | 355 | 200 | 236 | 264 |
| EP-PL-LYTE | 27.5 | 198 | 272 | 366 | 255 | 284 | 300 |

It can be seen in Table 2 that the platelet extract EP-95-11 of the present invention resulted in a more effective proliferation and a 3 to 4-fold increase in MTT as compared to the PTRF extract of Knighton.

Furthermore, the platelet extract EP-PL-LYTE, resulted in even more effective proliferation and more than 10-fold increase in MTT as compared to the PTRF extract of Knighton.

Thus, the lyophilisation step permits the easy storage of the extract and a lengthened shelf life. The Plasma Lyte with the lyophilisation allows for the preservation of the active principles in a non-denatured form (matured) and result in an increased concentration of the growth factors in each ml of extract.

Figure 3:
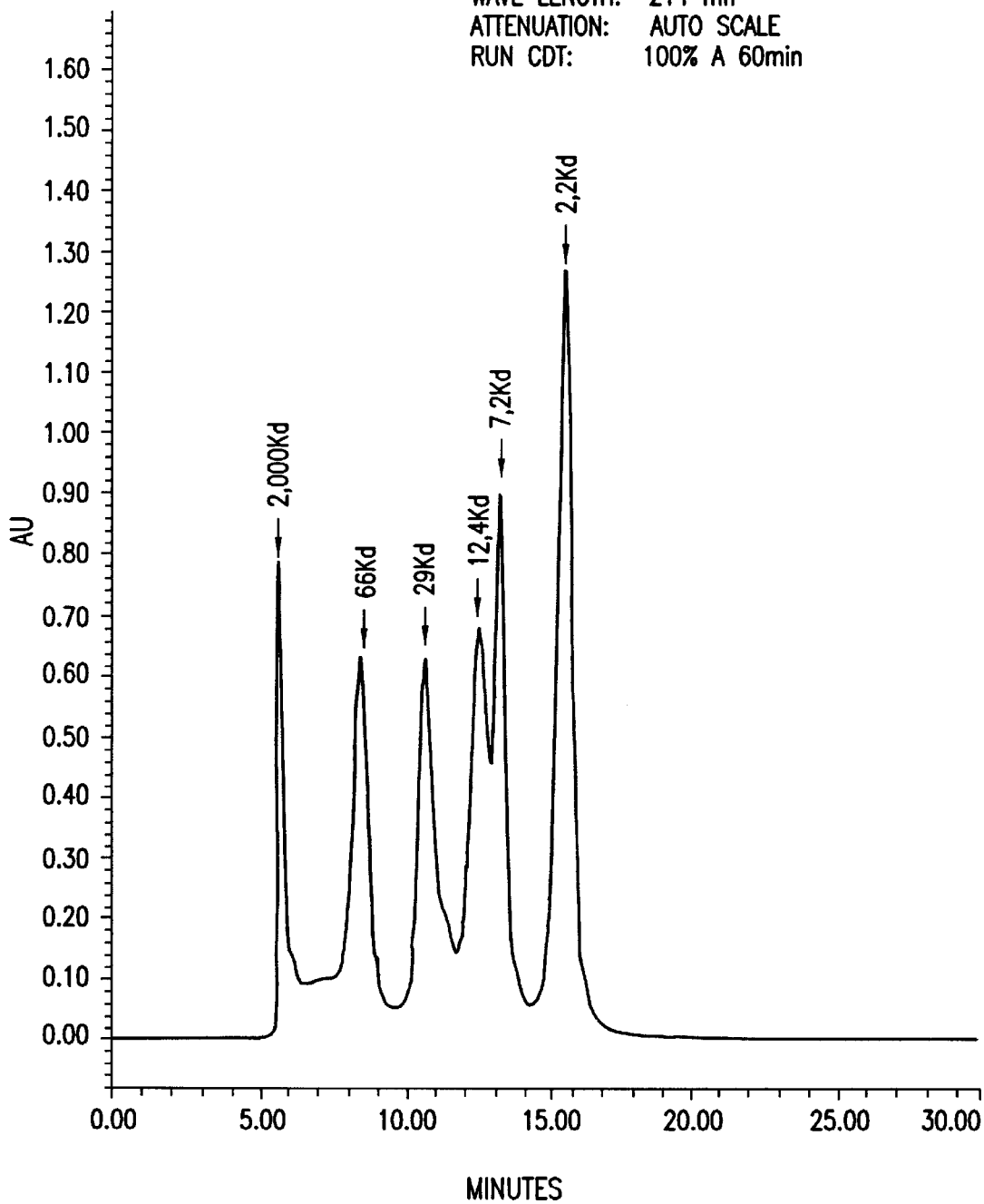
FIG. 3 illustrates the elution profile on column Protein Pak SW™ (8.0×300) of different molecular weight markers.

FIG. 3 illustrates the elution profile on column Protein Pak SW™ (8.0×300) of different molecular weight markers.

Figure 4:
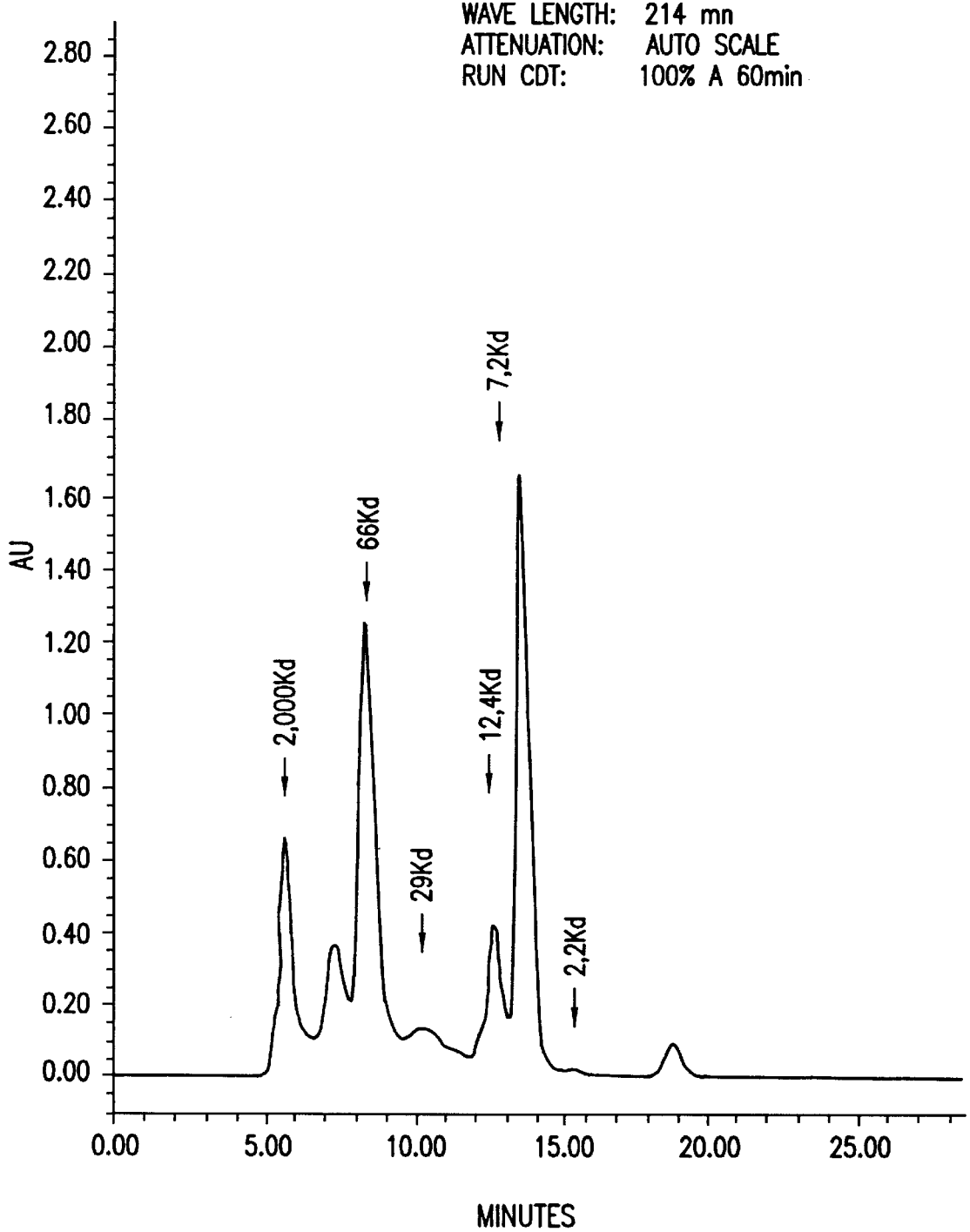
FIG. 4 illustrates the elution profile on column Protein Pak SW™ (8.0×300) of platelet reference (PTRF) according to the procedure of Knighton.
Figure 5:
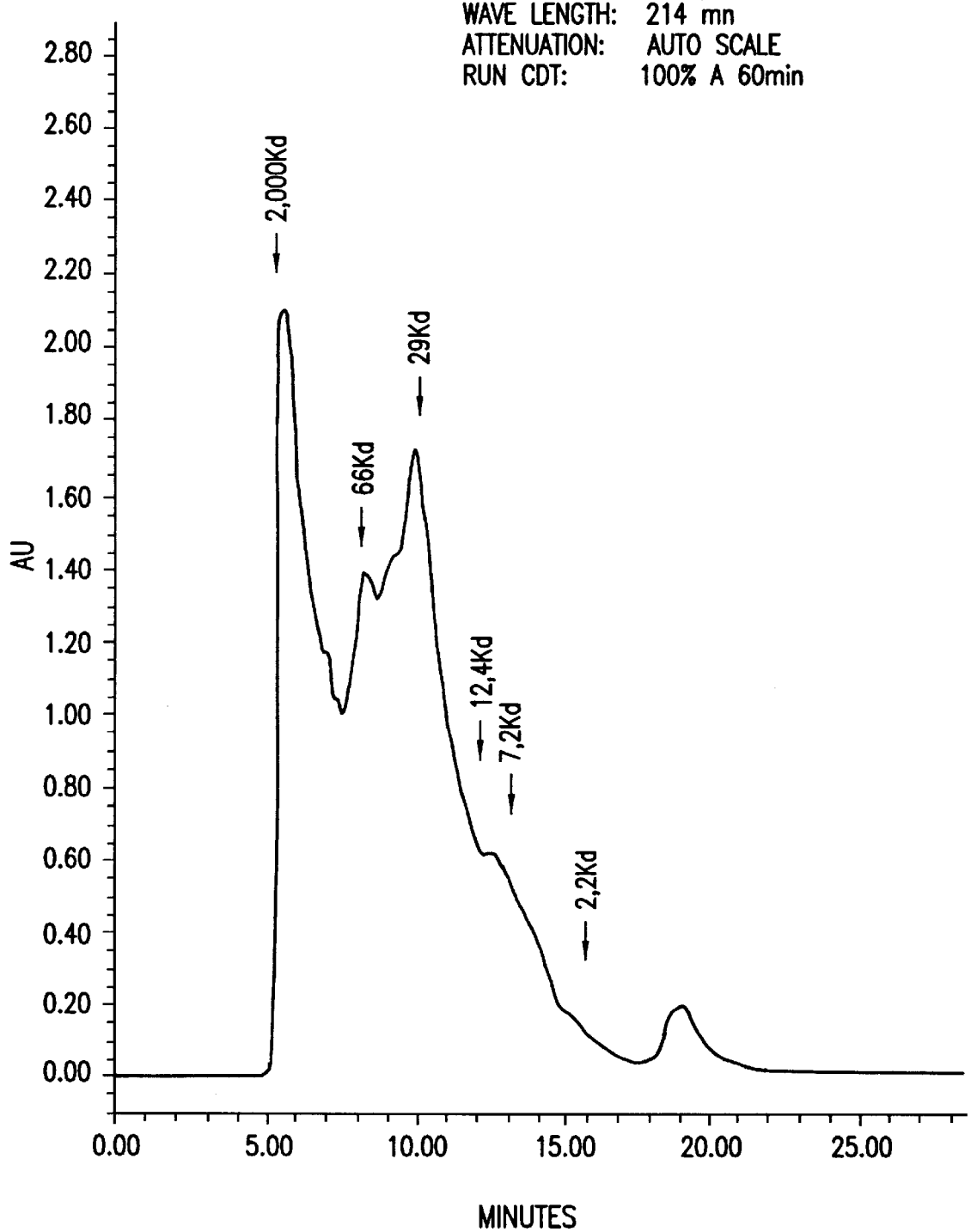
FIG. 5 illustrates the elution profile on column Protein Pak SW™ (8.0×300) of a porcine platelet extract (EP-PL-Lyte) in accordance with one embodiment of the present invention.
Figure 6:
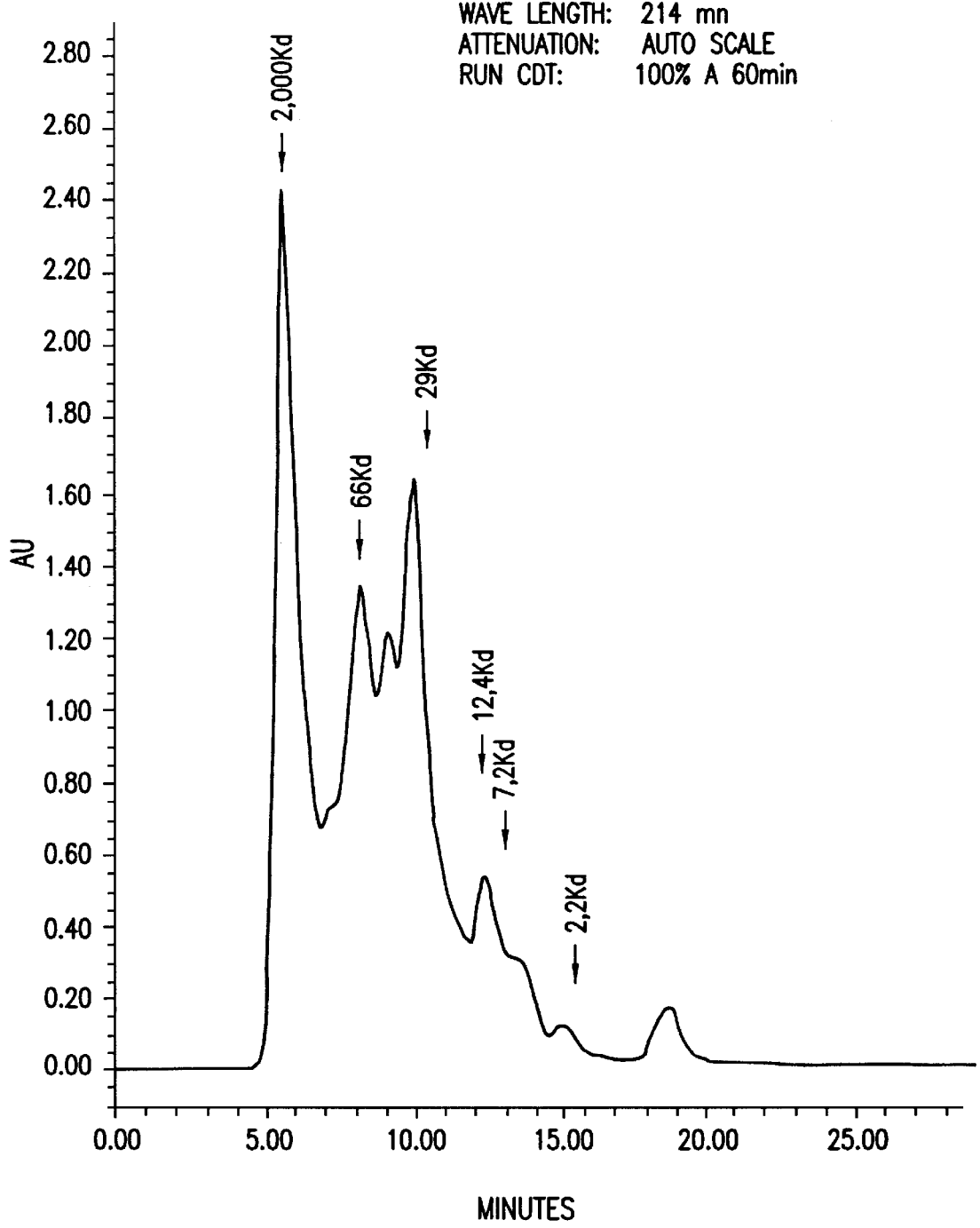
FIG. 6 illustrates the elation profile on column Protein Pak SW™ (8.0×300) of a porcine platelet extract (EP-95-11) in accordance with one embodiment of the present invention.
Figure 7:
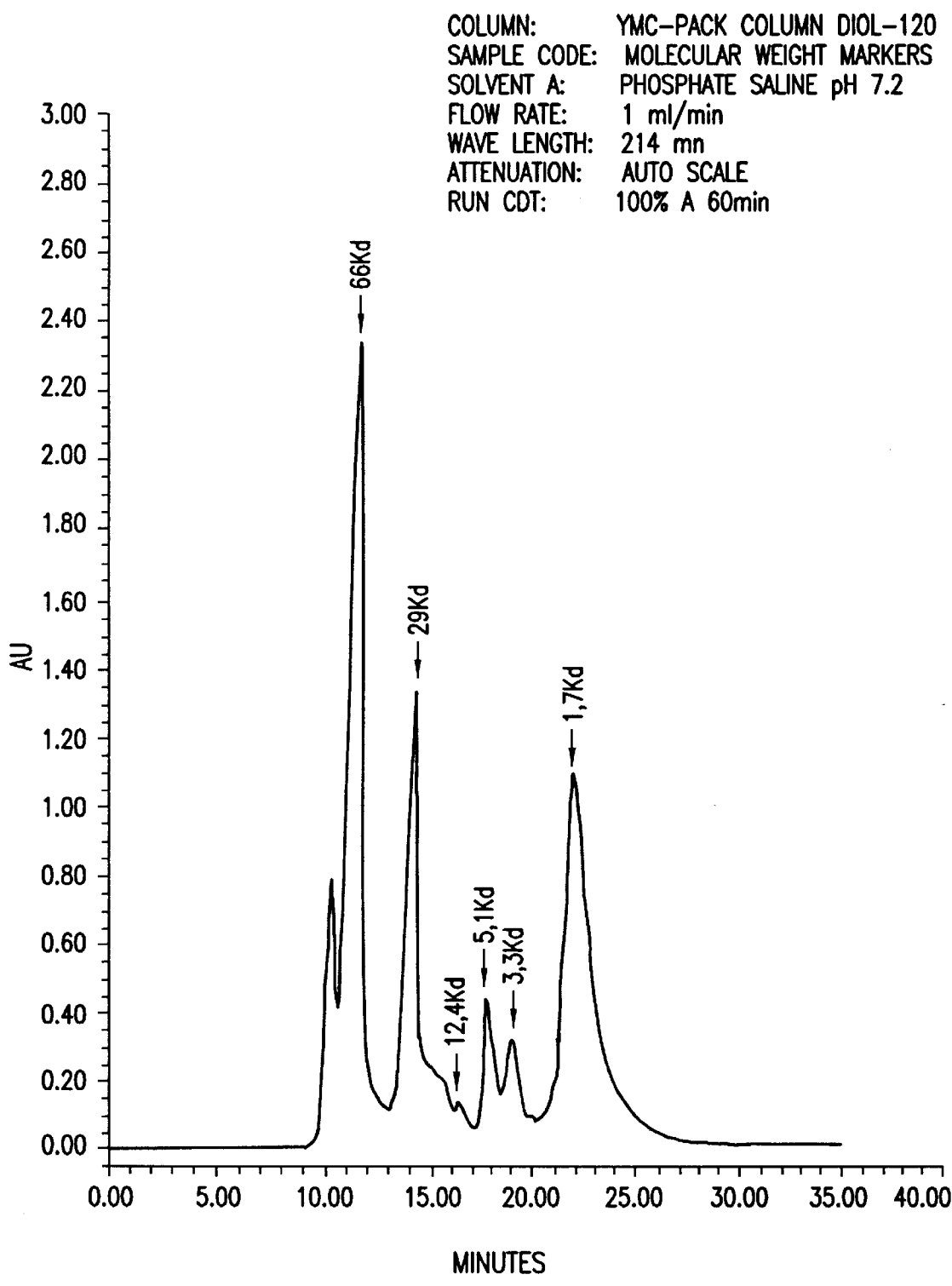
FIG. 7 illustrates the elution profile on YMC-Pak Column Diol-120™ of different molecular weight markers.
Figure 8:
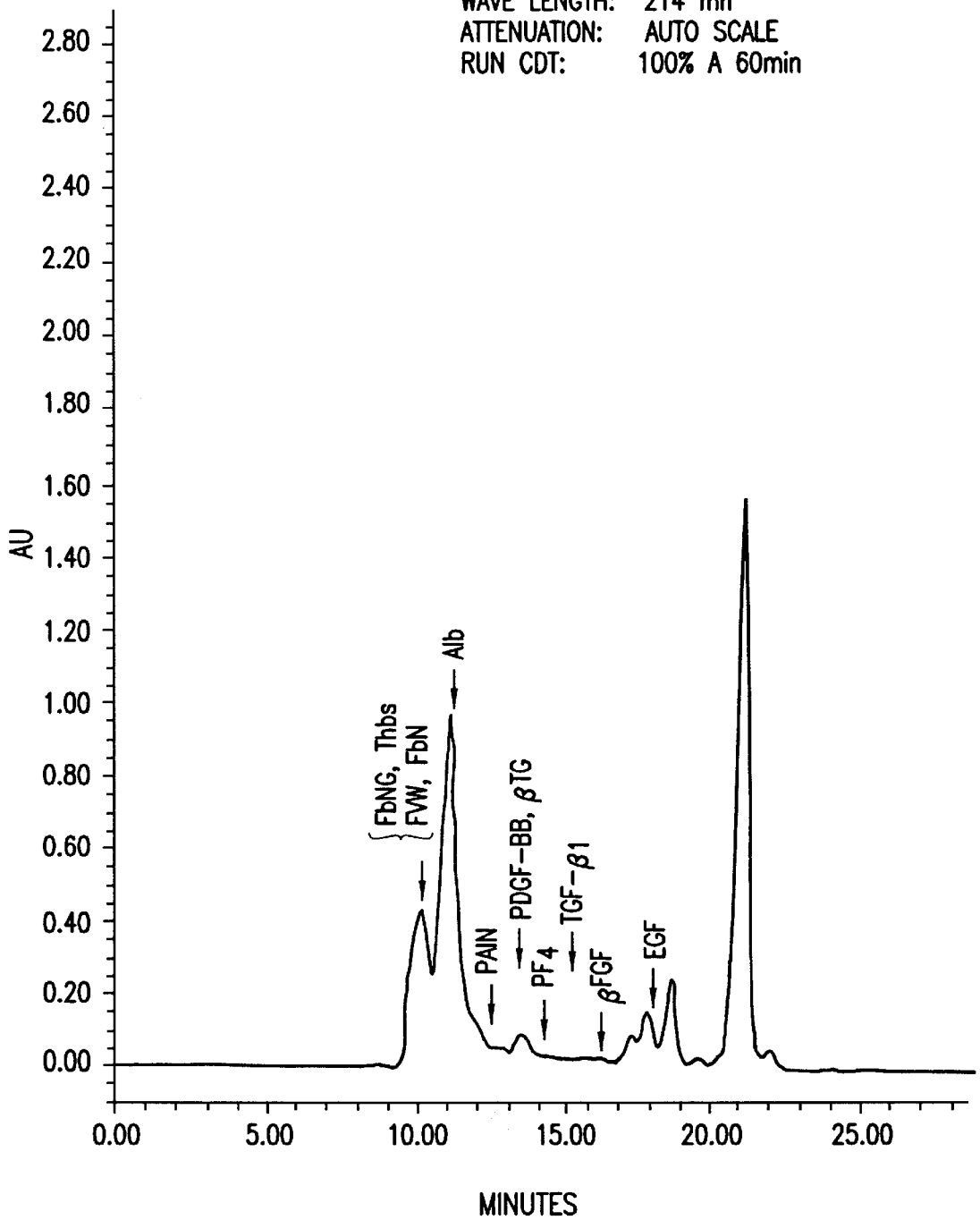
FIG. 8 illustrates the elution profile on YMC-Pak Column Diol-120™ of platelet reference (PTRF) according to the procedure of Knighton.
Figure 9:
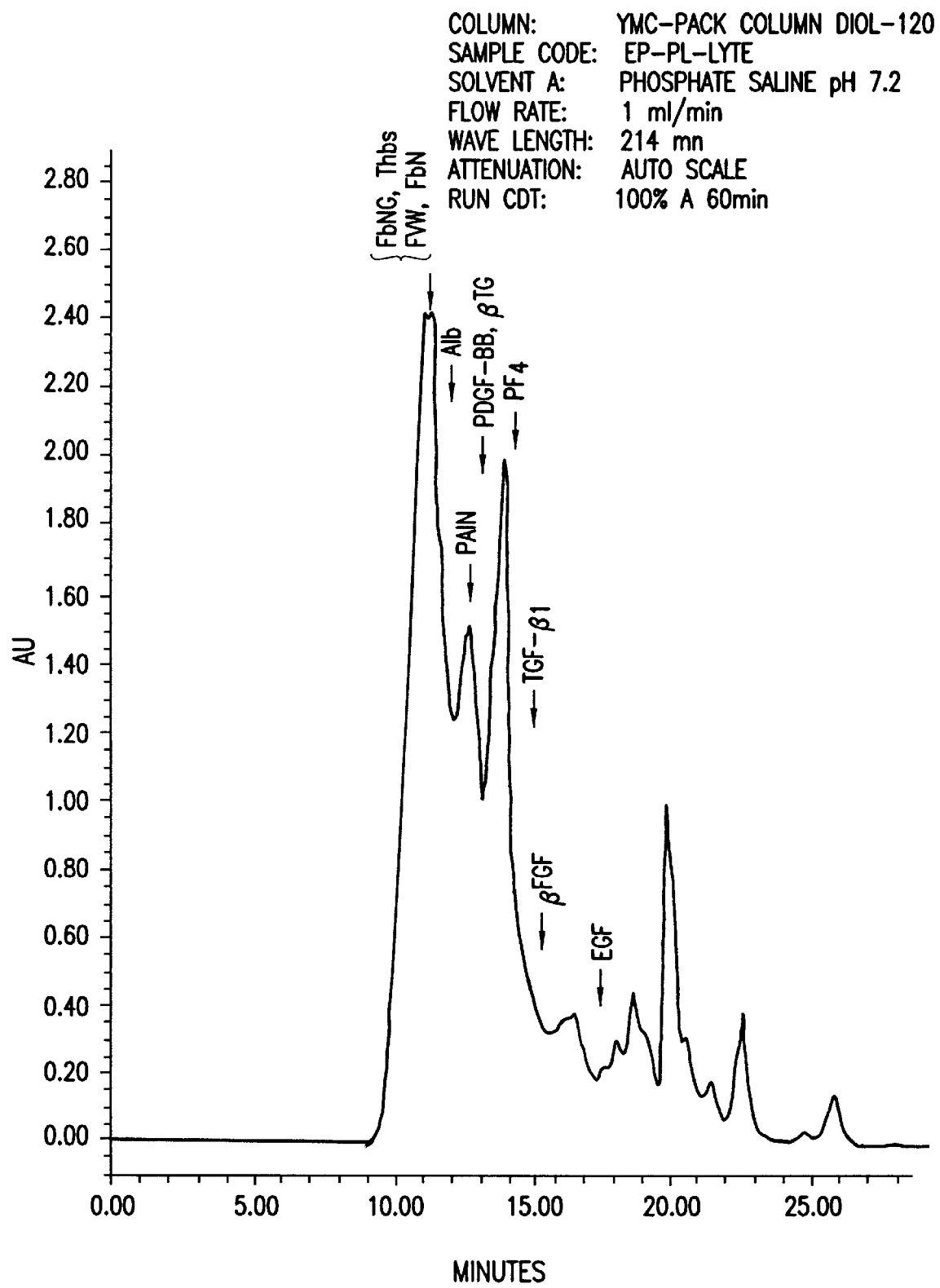
FIG. 9 illustrates the elution profile on YMC-Pak Column Diol-120™ of a porcine platelet extract (EP-PL-Lyte) in accordance with one embodiment of the present invention.
Figure 10:
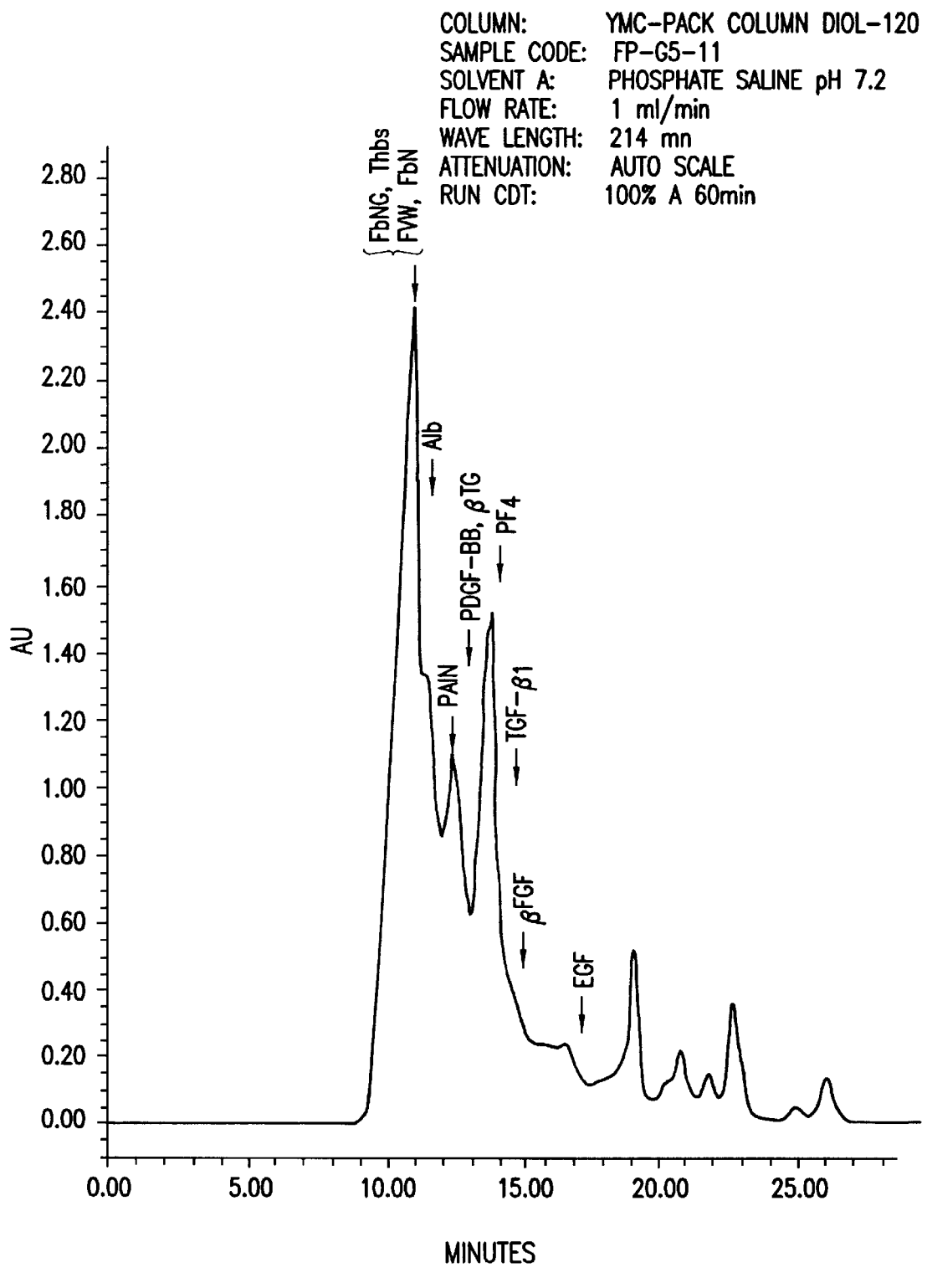
FIG. 10 illustrates the elution profile on YMC-Pak Column Diol-120™ of a porcine platelet extract (EP-95-11) in accordance with one embodiment of the present invention.

FIGS. 4 to 6 illustrate the results of a comparative analysis of elution profiles of the PTRF extract of Knighton as compared to EP-95-11 and EP-PL-LYTE platelet extracts of the present invention. These elution profiles were conducted on column Protein Pak SW™ (8.0×300).

FIGS. 7 to 10 illustrates a further comparative analysis of elution profile conducted on a different column YMC-Pak Column Diol-120™.

It can be seen from these comparative analyses that the extracts of the present invention show a higher concentration of the growth factors, based on direct measurements, which could explain the higher activity found in Table 2. Also, in both column systems, the concentration of proteins and growth factors is much higher than for the extract obtained by the process of Knighton.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A process for the preparation of porcine platelet-extract containing matured growth factors, thrombospondin, fibronectin and minimal albumin, which comprises the steps of:
   a) centrifuging whole porcine blood at about 1000 g to about 5000 g to isolate the platelets from the platelet-rich-plasma;
   b) resuspending the isolated platelets of step a) in Plasma-Lyte A and centrifuging to concentrate said platelets;
   c) washing said concentrated platelets of step b);
   d) lyophilizing said washed platelets of step c); whereby causing lysis of said platelets and producing the platelet extract.

2. The process of claim 1, which further comprises a step of resuspension after step d), wherein said lyophilized platelets are resuspended.

3. The process of claim 2, wherein said resuspension is effected in pure water.

4. The process of claim 1, wherein said washing of step c) is effected in pure water or in Plasma-Lyte A.

5. A pharmaceutical composition for promoting wound healing, which comprises an effective concentration of a platelet extract prepared according to the process of claim 1, wherein said platelet extract contains matured growth factors, thrombospondin, fibronectin and minimal albumin; in association with a pharmaceutically acceptable carrier.

6. The pharmaceutical composition of claim 5, wherein said platelet extract concentration is between $10^7$ to $10^{12}$ platelet equivalent/ml.

7. A method for the promotion of wound healing of a patient which comprises the topical administration of the composition of claim 5 on the wound of the patient.

8. A porcine platelet-extract prepared according to the process of claim 1, which comprises matured growth factors, thrombospondin, fibronectin and traces of albumin proteins.

* * * * *